United States Patent [19]

Edwards, III et al.

[11] 4,163,856

[45] Aug. 7, 1979

[54] AZETIDINE COMPOUNDS AND PROCESS FOR PRODUCTION

[75] Inventors: William B. Edwards, III, Richmond; Henry V. Secor, Midlothian, both of Va.; Norman H. Cromwell, Lincoln, Nebr.

[73] Assignee: Philip Morris Incorporated, New York, N.Y.

[21] Appl. No.: 889,188

[22] Filed: Mar. 23, 1978

Related U.S. Application Data

[62] Division of Ser. No. 590,670, Jun. 26, 1975, abandoned.

[51] Int. Cl.$^2$ .............................................. C07D 401/02
[52] U.S. Cl. ................................ 546/329; 260/239 A
[58] Field of Search ...................... 260/296 R, 239 AR

[56] References Cited

PUBLICATIONS

Testa et al., Chem. Abstracts, vol. 57, col. 15039 (1962).

Secor et al., Chem. Abstracts, vol. 86, abst. 120778g (1977).

Chem. Abstracts, Subject Index, vol. 86, p. 4535CS (1977).

Klingsberg, Pyridine and Its Derivatives, Part One, pp. 2-3, Interscience Publishers, NY (1960).

*Primary Examiner*—John D. Randolph
*Attorney, Agent, or Firm*—Watson, Leavenworth, Kelton & Taggart

[57] ABSTRACT

Novel azetidine, and particularly 3-pyridyl-azetidine, compounds are disclosed. These compounds are produced from γ-amino alcohols by a sequence comprising disulfonation to produce the sulfonamido-alkylsulfonate and then cyclization to the N-sulfonylazetidine. These azetidine compounds may then be transformed, as desired, to various N-derivatives by substitution of hydrogen or other univalent organic groups on the secondary amine of the azetidine ring.

4 Claims, No Drawings

AZETIDINE COMPOUNDS AND PROCESS FOR PRODUCTION

This is a division of application Ser. No. 590,670, filed June 26, 1975, now abandoned.

BACKGROUND OF THE INVENTION

Numerous azetidine compounds are known in the art and are credited with a spectrum of utilities. One such use derives from the relationship between azetidine and ethylenimine. The alkylating action evidenced by both of these compounds, and the effectiveness of the latter in various therapeutic schemes, has stimulated substantial investigation of azetidine analogs of ethylenimine derivatives of known clinical use for the control of neoplastic disease.

Azetidine compounds have also been successful as reagents in the well-known Vilsmeier-Haack reaction. There, it is azetidine amides which have been utilized.

The foregoing and other investigations have, however, been severely hampered by the low number of azetidine compounds available in the prior art. This scarcity is in turn dependent upon the prior art methods for producing such compounds. These methods permit the synthesis of relatively few azetidine compounds.

One such prior art method for producing azetidine compounds involves cyclization of amino-esters by treatment with a Grignard reagent to yield azetidinones ($\beta$-lactams) which may then be reduced with lithium aluminum hydride to yield the azetidine. This reaction has been successful, however, only where the amino ester is limited in its substituents. Consequently it has not proven useful for the production of many desired compounds.

DESCRIPTION OF THE INVENTION

The present invention relates to a novel process for making azetidine compounds and to certain novel chemical compounds thereby produced. More particularly, this invention involves a process for transforming $\gamma$-amino alcohols into useful azetidine compounds, including novel 3-substituted-azetidine compounds.

These azetidine compounds of the present invention are produced from $\gamma$-amino alcohols having the formula:

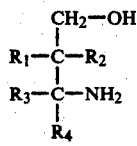

Wherein:
Each of $R_1$ and $R_2$ is hydrogen, alkyl, aryl, arylalkyl, heteroaromatic, or alkylheteroaromatic; and
each of $R_3$ and $R_4$ is hydrogen, alkyl, aryl or alylalkyl.

As utilized herein the description of the present invention, alkyl means an alkyl group of from 1 to 10, preferably from 1 to 2, carbons. Aryl means an aromatic such as phenyl, tolyl, chlorophenyl, or naphthyl. Arylalkyl means a group such as benzyl. Heteroaromatic means pyridyl, furanyl and the like. By alkylheteroaromatic, it is meant the analogs of the alkyl aromatics such as picolyl.

In referring to aromtic ring configurations, substituents are not excluded. The degree of substitution permitted includes alkyl, cycloalkyl, aryl, arylalkyl, alkyl-heteroaromatic, heteroaromatic, and halogen at any of the available carbons of the ring. Acid addition salts of heteroaromatics and alkylheteroaromatics, such as the hydrochloride, are also included.

The scope of this invention is not restricted by the substituents on the $\gamma$-amino alcohol. These substituents may, however, result in some retardation in the rate of the reactions for the production of azetidine compounds. Consequently, in a particularly preferred embodiment of the present invention, at least one of $R_3$ and $R_4$ is hydrogen. In a still more preferred embodiment, $R_1$ or $R_2$ is also hydrogen, the other being pyridyl or a substituted pyridyl.

$\gamma$-amino alcohols useful in accordance with the present invention are available commercially. These amino alcohols, or corresponding derivatives thereof within the scope of the foregoing formula, may be utilized as the starting material for the present process.

The present process is also inclusive of starting materials which are novel in the art. These $\gamma$-amino alcohols are ones having $\alpha$-, $\beta$-, or $\gamma$-substituents, particularly $\beta$-pyridyl or substituted $\beta$-pyridyl substituents. These novel starting materials may be produced by means set forth in U.S. application Ser. No. 590,669 entitled "Gamma-Amino Alcohols And Method For Production" of Henry V. Secor filed on the same date as this application. Accordingly, and further to describe means for producing the present starting material, this application is incorporated by reference herein as if it were set forth at length.

In order to place the amino alcohols in a form from which they can be cyclized into the azetidine ring structure, it is necessary first to convert both the alcohol and the amine groups into reactive form. This may be done by sulfonating each of these groups, so as to produce the sulfonamide on the one hand and the sulfonate on the other. Suitable reagents for effecting this step are radicals having the formula: $-SO_2R$.

In this formula, R may be alkyl, aryl, or aryl alkyl. It is most preferred that the reagent be a tosyl radical, most preferably p-tosyl. Exemplary reagent compounds with which the amino alcohol may be activated are the toluenesulfonyl halides such as p-tosyl cloride and p-tosyl bromide.

This activation may be performed by a straightforward reaction of the amino alcohol with a suitable reagent such as tosyl chloride. This reaction is normally performed utilizing a mole ratio of approximately 2:1 of sulfonating reagent to amino alcohol, respectively. This reaction should be performed in a suitable solvent, preferably a mildly basic organic solvent such as pyridine. The 3-sulfonamido-alkylsulfonates are produced at between 25° C. and the solvent freezing point, most preferably at $-10°$ to 10° C., over from one to for days.

Cyclization is performed by cleavage of the sulfonate radical from the sulfonamido-alkylsulfonate. This cleavage, and the resultant cyclization may be performed by means known in the art. Exemplary of these means are the techniques set forth in Vaughan et al, *Journal of Organic Chemistry*, 26, 138 (1961). Most preferably, however, the cleavage and cyclization is performed utilizing potassium t-butoxide in a solution of t-butyl alcohol. The product of this cyclization is N-sulfonylazetidine, most preferably, p-toluenesulfonylazetidine.

This N-sulfonylazetidine, having substituents corresponding to those set forth hereinabove for the starting material γ-amino alcohol, may then in turn be reduced to produce an N-hydrogen azetidine compound. Any suitable reducing agent may be utilized for conversion of the N-sulfonylazetidine. Exemplary is sodium naphthalenide. During treatment, it is also desirable that a proton donor such as t-butanol be present to facilitate the conversion. Thus the combination of a suitable reducing agent and a proton donor provides a significantly increased yield of N-hydrogen-azetidine compound. Again low temperature is desirable, with from −70° to −40° C. being preferred. The reaction is virtually instantaneous.

In an additional embodiment, this azetidine may be alkylated to form the N-alkyl-azetidine. These compounds are similar in utility and may readily be produced by means known in the art. Thus, for example, N-methyl-azetidine compounds are produced in good yield by treatment of the N-hydrogen-azetidine with formaldehyde and formic acid in aqueous medium.

As set forth above, there are numerous utilities for the azetidine compounds are substituted azetidines of this invention. In addition, however, reference is made to U.S. Pat. Nos. 3,076,799 of Testa et al; 3,124,569 of Testa et al, and French Pat. No. 624,575 of Calanda-Stiftung. These indices of the prior art exemplify various of the specific uses to which these valuable products have been put.

As previously indicated, certain products of the present invention are also novel and not believed producible by means otherwise known in the art. These compounds comprise the 3-substituted, and particularly the 3-pyridyl-azetidines and derivatives thereof. These novel compounds have the formula:

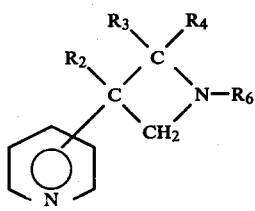

Wherein:

$R_2$, $R_3$, and $R_4$ are identically as set forth above with respect to the amino alcohol precursors; and $R_6$ is hydrogen or alkyl, most preferably either hydrogen or methyl.

As indicated by the formula, the point of bonding between the pyridyl and azetidine groups is not critical. Ordinarily, however, the 3-pyridyl group is preferred. Also permissible, are substituents on the pyridyl group. Any of the four available valences may be satisfied by hydrogen, halogen, alkyl, aryl, alkylaryl, cycloalkyl, heteroaromatic, or alkyl heteroaromatic constituents. Further, this formula includes pyridyl or substituted pyridyl addition salts such as the hydrochloride.

These novel compounds have utilities similar to those of the azetidines in general and as already described. In addition, however, they have been discovered to be useful as pesticides.

As such, they may be applied, ordinarily dissolved in a suitable solvent—for example, as a 1% aqueous solution—to plants infested with pests such as spider mites. It has been discovered that they are ordinarily useful not only against adult, but also nymph, form of such pests.

The present invention will be more apparent from the following. This exemplification is intended to illustrate this invention and is not limitative of its scope.

EXAMPLE 1

3-amino-2-(3-pyridyl)-1-propanol was prepared by the process set forth in the aforementioned U.S. application Ser. No. 590,669 of Henry V. Secor, 35.2 g (0.23 mole) of this γ-amino alcohol was stirred into 335 ml of dry pyridine and the solution cooled to −5° C. 96.9 g (0.509 moles) of p-tosyl chloride was then added in portions to the solution. The solution was stirred in an ice bath for 2 hours, after which it was diluted to 3 liters with ice water and refrigerated at 4° C. overnight. Oil separated and solidified after vigorous scratching. The solid was collected, washed with water and dried at reduced pressure to yield 66.5 g (62.5% yield) of dark red 2-(3-pyridyl)-3-(p-toluenesulfonamido)propyl-p-toluenesulfonate of melting point 150°–153° C.

This sulfonamido-sulfonate was then added to a reagent, produced by adding 6.25 grams (0.16 mole) of clean potassium metal to 6.5 liters of t-butanol, which had been refluxed for 1.5 hours. Addition was made at 30° C. and the solution stirred and heated under reflux for 10 hours. This solution was cooled slightly and treated with 20 grams of activated carbon and refluxed for one additional hour partially to effect purification. The solution was filtered and solvent removed to give 32.0 g. (77%) of crude solid which was then chromatographed on one kilogram of silica gel. Elution with 10% acetone in benzene afforded 21.2 g of tan solid which was again treated with activated carbon, followed by trituration with ether.

The product, 3-(3-pyridyl)-p-toluenesulfonylazetidine was obtained in a yield of about 37%. mp 95°–96.5°; ir (Nujol) 1155 and 1340 cm$^{-1}$ (NSO$_2$); nmr (CDCl$_3$) δ 2.5 (s,3,CH$_3$), 3.95 (m,5), 7.35 (m,4), 7.8 (m,2), 8.4 (m,2); mass spectrum m/e (rel. intensity) 288 (0.5,M+), 65 (14.6), 106 (22.2), 196 (25.7), 91 (29.9), 105 (100).

Anal. Calcd. for C$_{15}$H$_{16}$N$_2$SO$_2$: C, 62.47; H, 5.59; N, 9.71; S, 11.12. Found: C, 62.55; H, 5.47; N, 9.70; S, 11.18.

EXAMPLE 2

18.4 grams (64 mmole) of the 3-(3-pyridyl)-p-toluenesulfonylazetidine produced in accordance with Example 1 was added to a solution of 4.7 g (64 mmoles) of t-butanol and 1 liter of glyme. After briefly heating to 50° C. and with stirring in an argon atmosphere to effect complete solution, the temperature was lowered to −60° C. and a previously prepared sodium naphthalenide solution was added over a 2-hour period keeping a temperature of the reaction medium between −60° and −65° C. 60 ml of methanol was then added to the reaction and left standing at room temperature overnight. This solution was filtered, concentrated to a small volume under reduced pressure and the residue taken up in petroleum ether and again filtered. The clear, off-colored petroleum ether filtrate was extracted with five 20 ml aliquots of water and the combined water extracts concentrated under reduced pressure to 20 ml of naphthalene-free solution of product. The solution was then dried by azeotropic distillation using benzene and ethanol to give a benzene solution of product. Distillation in vacuo gave a clear cut of 3-(3-pyridyl)-azetidine, 1.9 g (25%), bp 93°–97°/0.15 mm; ir (neat) 3300 (NH), 1576, 1482, 1428 cm$^{-1}$; nmr (CdCl$_3$) δ 2.04 (s, 1, NH), 3.94

(m, 5H, aliphatic ring), 7.18 (dd, J=4Hz, 1), 7.71 (dt, J=2Hz, 1), 8.5 (m, 2); mass spectrum m/e (rel. intensity) 134 (3.7, M+), 78 (18), 104 (33.3), 105 (100).

The yellow dipicrate was obtained in EtOH and recrystallized from water, mp 200°–201°.

Anal. Calcd. for $C_{20}H_{16}N_8O_{14}$: C, 40.55; H, 2,.72; N, 18.92. Found: C, 40.30: H, 2.82; N, 18.74.

EXAMPLE 3

660 mg (8.83 mmoles) of 40% by weidht aqueous formaldehyde in 9 ml of water and 755 mg (14.5 mmoles) of formic acid in 9 ml of water was then added to 920 mg (6.88 mmoles) of 3-(3-pyridyl)-acetidine produced in accordance with Example 2. After heating on a steam bath for 2 hours, cooling to 0° C. and adding 1.2 g (14.4 mmoles) of sodium bicarbonate, the solution was concentrated at reduced pressure to 7 ml. It was then dried by azeotroping in benzene and ethanol to give a dry benzene solution containing insolubles which were filtered off to yield N-methyl-3-(3-pyridyl)-azetidine.

Short path vacuum distillation gave one cut of clear colorless product 700 mg (58.5%), bp 63°–65°/0.15 mm; ir (neat) 2780 (NCH₃), 1577, 1483, 1429 cm⁻¹ (3-Py); nmr (CDCl₃) δ 2.37 (s, 3, CH₃), 3.16 (m,2), 3.70 (m,3), 7.15 (dd, J=4Hz, 1), 7.7 (dt, J=2Hz,1), 8.46 (m,2); mass spectrum m/e (rel. intensity) 148 (13.0, M+), 104 (34.9), 106 (73.0), 105 (100).

The dipicrate was obtained in EtOH and recrystallized from water, mp 191°–192°.

Anal. Calcd. for $C_{21}H_{18}N_8O_{14}$: C, 41.44; H, 2.90; N, 18.50. Found: C, 41.24; H, 2.92; N, 18.58.

We claim:
1. An azetidine compound having the formula

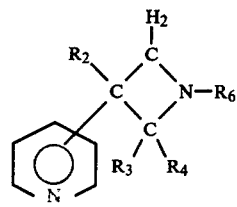

wherein:
$R_2$ is hydrogen or alkyl;
Each of $R_3$ and $R_4$ are hydrogen or alkyl; and
$R_6$ is hydrogen or alkyl.

2. The azetidine compound of claim 1, wherein $R_6$ is hydrogen or methyl.

3. The azetidine compound of claim 2, wherein $R_2$ is hydrogen.

4. The azetidine compound of claim 1, in which the pyridyl group is a 3-pyridyl group.

* * * * *

UNITED STATES PATENT OFFICE
CERTIFICATE OF CORRECTION

PATENT NO. : 4,163,856
DATED : August 7, 1979
INVENTOR(S) : William B. Edwards, III, Henry V. Secor and Norman H. Cromwell It is certified that error appears in the above-identified patent and that said Letters Patent are hereby corrected as shown below:

Column 2, line 55, "for" should read --four--.

Column 3, line 21, "are" should read --and--.

Column 5, line 10, "weidht" should read --weight--.

Signed and Sealed this

Sixth Day of November 1979

[SEAL]

Attest:

RUTH C. MASON
Attesting Officer

LUTRELLE F. PARKER
Acting Commissioner of Patents and Trademarks